(12) United States Patent
Huter

(10) Patent No.: US 6,569,184 B2
(45) Date of Patent: May 27, 2003

(54) RECOVERY SYSTEM FOR RETRIEVING AN EMBOLIC PROTECTION DEVICE

(75) Inventor: Benjamin C. Huter, Murrieta, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 259 days.

(21) Appl. No.: 09/796,226

(22) Filed: Feb. 27, 2001

(65) Prior Publication Data

US 2002/0120287 A1 Aug. 29, 2002

(51) Int. Cl.⁷ .............................................. A61M 29/00
(52) U.S. Cl. ..................................................... 606/200
(58) Field of Search ................................. 606/200, 191, 606/198, 192, 194, 195, 197, 159, 127, 108; 604/104, 105, 106, 107, 108; 128/898

(56) References Cited

U.S. PATENT DOCUMENTS

| | | |
|---|---|---|
| 3,952,747 A | 4/1976 | Kimmell, Jr. |
| 4,425,908 A | 1/1984 | Simon |
| 4,494,531 A | 1/1985 | Gianturco |
| 4,612,931 A | 9/1986 | Dormia |
| 4,619,246 A | 10/1986 | Molgaard-Nielsen et al. |
| 4,643,184 A | 2/1987 | Mobin-Uddin |
| 4,650,466 A | 3/1987 | Luther |
| 4,662,885 A | 5/1987 | DiPisa, Jr. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gerwertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |

(List continued on next page.)

FOREIGN PATENT DOCUMENTS

| | | |
|---|---|---|
| EP | 0 472 334 A1 | 2/1992 |
| GB | 2020557 | 11/1997 |
| WO | WO92/03097 | 3/1992 |
| WO | WO96/01591 | 1/1996 |
| WO | WO97/17100 | 5/1997 |
| WO | WO98/02084 | 1/1998 |
| WO | WO98/33443 | 8/1998 |
| WO | WO99/23976 | 5/1999 |

*Primary Examiner*—A. Vanatta
(74) *Attorney, Agent, or Firm*—Fulwider Patton Lee & Utecht, LLP

(57) ABSTRACT

A system for recovering an embolic protection device having an expandable filter disposed on a guide wire includes an inner catheter loaded inside a recovery sheath. The inner catheter has a distal portion which extends beyond the distal end of the recovery sheath when the recovery system is being advanced over the guide wire of the embolic protection device. The inner catheter has more flexibility than the recovery sheath, and enhances delivery through tortuous anatomy to the location of the deployed filter. Once the recovery system is advanced in close proximity to the expandable filter of the embolic protection device, the recovery sheath is advanced over distal portion of the inner catheter and over the expandable filter to collapse the filter for removal from the body vessel. The recovery sheath has sufficient column strength to collapse the expanded filter for removal from the body vessel.

17 Claims, 2 Drawing Sheets

U.S. PATENT DOCUMENTS

| | | |
|---|---|---|
| 5,064,428 A | 11/1991 | Cope et al. |
| 5,071,407 A | 12/1991 | Termin et al. |
| 5,092,839 A | 3/1992 | Kipperman |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,160,342 A | 11/1992 | Reger et al. |
| 5,192,286 A | 3/1993 | Phan et al. |
| 5,324,304 A | 6/1994 | Rasmussen |
| 5,329,942 A | 7/1994 | Gunther et al. |
| 5,330,482 A | 7/1994 | Gibbs et al. |
| 5,350,398 A | 9/1994 | Pavcnik et al. |
| 5,370,657 A | 12/1994 | Irie |
| 5,383,887 A | 1/1995 | Nadal |
| 5,421,832 A | 6/1995 | Lefebvre |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,549,626 A | 8/1996 | Miller et al. |
| 5,601,595 A | 2/1997 | Smith |
| 5,626,605 A | 5/1997 | Irie et al. |
| 5,634,942 A | 6/1997 | Chevillon et al. |
| 5,649,953 A | 7/1997 | Lefevre |
| 5,662,671 A | 9/1997 | Barbut et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,772,674 A | 6/1998 | Nakhjavan |
| 5,779,716 A | 7/1998 | Cano et al. |
| 5,792,145 A | 8/1998 | Bates et al. |
| 5,792,156 A | 8/1998 | Perouse |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,650 A | 11/1998 | Imran |
| 5,836,868 A | 11/1998 | Ressemann et al. |
| 5,846,251 A | 12/1998 | Hart |
| 5,846,260 A | 12/1998 | Maahs |
| 5,848,965 A | 12/1998 | Samuels |
| 5,868,708 A | 2/1999 | Hart et al. |
| 5,876,367 A | 3/1999 | Kaganov et al. |
| 5,897,567 A | 4/1999 | Ressemann et al. |
| 5,910,154 A | 6/1999 | Tsugita et al. |
| 5,911,734 A | 6/1999 | Tsugita et al. |
| 5,941,896 A | 8/1999 | Kerr |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A | 12/1999 | Daniel et al. |
| 6,013,093 A | 1/2000 | Nott et al. |
| 6,152,946 A | 11/2000 | Broome et al. |
| 6,165,200 A * | 12/2000 | Tsugita et al. ............... 606/200 |
| 6,171,327 B1 | 1/2001 | Daniel |
| 6,179,859 B1 | 1/2001 | Bates et al. |
| 6,251,122 B1 * | 6/2001 | Tsukernik ................... 606/200 |
| 6,306,163 B1 * | 10/2001 | Fitz .......................... 623/1.12 |
| 6,361,546 B1 * | 3/2002 | Khosravi ..................... 606/200 |
| 6,364,895 B1 * | 4/2002 | Greenhalgh .................. 606/200 |
| 6,383,206 B1 * | 5/2002 | Gillick et al. ............... 606/200 |
| 2002/0042626 A1 * | 4/2002 | Hanson et al. .............. 606/200 |
| 2002/0169474 A1 * | 11/2002 | Kusleika et al. ............ 606/200 |

* cited by examiner

RECOVERY SYSTEM FOR RETRIEVING AN EMBOLIC PROTECTION DEVICE

BACKGROUND OF THE INVENTION

The present invention relates generally to a system which can be used when an interventional procedure is being performed in a stenosed or occluded region of a blood vessel to capture embolic material that may be created and released into the bloodstream during the procedure. The system of the present invention is particularly useful when performing balloon angioplasty, stenting procedures, laser angioplasty or atherectomy in critical vessels, such as the carotid arteries, where the release of embolic debris into the bloodstream can occlude the flow of oxygenated blood to the brain or other vital organ. It is to be understood that the system and method of this invention can be used in numerous other vascular interventional procedures.

Numerous procedures have been developed for treating occluded blood vessels to allow blood to flow without obstruction. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the size of the blood vessel.

Another procedure is laser angioplasty which utilizes a laser to ablate the stenosis by super heating and vaporizing the deposited plaque. Atherectomy is yet another method of treating a stenosed blood vessel in which a cutting blade is rotated to shave the deposited plaque from the arterial wall.

In another widely practiced procedure, the stenosis can be treated by placing a device known as a stent into the stenosed region to hold open and sometimes expand the segment or blood vessel or other arterial lumen. Stents are particularly useful in the treatment or repair of blood vessels by percutaneous transluminal coronary angioplasty (PTCA), percutaneous transluminal angioplasty (PTA) or removal by atherectomy or other means. Stents are delivered in a compressed condition to the target site, and then are deployed at the target location into an expanded condition to support the vessel.

In the process of treating lesions in the blood vessels, release of plaque (embolic debris) may possibly occur during the treatment. Detached from the lesion, the embolic debris enters the bloodstream and subsequently migrate through the patient's vasculature. Larger embolic debris can obstruct a vessel and cause ischemia, apoptosis, or vessel necrosis.

To allow the use of more aggressive treatment of vascular lesions, procedures have also been developed for capturing embolic debris flowing through the vessels with the blood. One approach involves the placement of a filter downstream from the treatment site to capture embolic debris before it reaches the smaller blood vessels downstream. The placement of a filter in the patient's vasculature during treatment of the vascular lesion can reduce the presence of the embolic debris in the bloodstream. Such filters are usually delivered in a collapsed position through the patient's vasculature and then expanded to trap the embolic debris. Once the procedure is completed, the filter can be collapsed, and the filter (with the trapped embolic debris) can then be removed from the vessel. While a filter can be effective in capturing embolic material, the filter still needs to be collapsed and removed from the vessel. During this procedure, it is important that the captured embolic debris remain trapped within this filter so that particles are not released back into the body vessel. Additionally, the recovery apparatus should be relatively flexible to avoid straightening the body vessel. Recovery devices which are too stiff can cause trauma to the vessel walls as the filter is being collapsed and removed from the vasculature.

There is a need in the art for an apparatus and method which can collapse a deployed filter containing captured embolic material for removal from the vasculature. Such an apparatus and method should be capable of being delivered through tortuous anatomy to the desired treatment site, and avoid straightening of the vasculature during delivery. Such an apparatus and method should be easy and safe to deploy, and be easily removed from the vasculature with minimal adverse impact or immunological response to the patient.

SUMMARY OF THE INVENTION

The present invention is directed to embolic protection systems having reduced stiffness characteristics. The recovery system of the present invention can be used to recovery an embolic protection device which generally includes a guide wire having a distal end and an expandable filter located near the distal end of the guide wire. The recovery system utilizes an inner catheter which is capable of being introduced over the guide wire, along with a recovery sheath that extends co-axially over the inner catheter. The inner catheter is capable of being loaded inside a lumen of the recovery sheath. In use, a distal portion of the inner catheter extends beyond the distal end of the recovery sheath allowing the inner catheter to initially approach the expandable filter which has been deployed within the patient's vasculature. In one aspect of the present invention, the distal portion of the inner catheter can initially extend approximately ten to fifteen centimeters, or more, beyond the distal end of the recovery sheath during initial delivery within the patient's vasculature. Thereafter, once the inner catheter has been placed near the expandable filter, the recovery sheath can then be advanced up over the inner catheter to collapse the expandable filter as the recovery sheath advances over the expandable filter. Thus, during delivery, the composite embolic protection recovery system has reduced stiffness characteristics at the distal end since the more flexible distal portion of the inner catheter extends beyond the recovery sheath. This reduced stiffness improves tracking over the guide wire through the patient's vasculature and also helps to avoid the tendency of curved vasculature to "straighten" due to the presence of a somewhat stiff recovery sheath. In this regard, the inner catheter, which has a smaller diameter and can be more flexible by having less column strength than the recovery sheath, initially tracks through the vasculature allowing the patient's vasculature to first conform to the inner catheter, rather than being "straightened" due to the presence of a stiffer recovery sheath. The inner catheter could also have high column stiffness, but be relatively easily bent radially, as if a polyimide were being used. Thereafter, the patient's vasculature will be less likely to straighten as the recovery sheath is advanced over the inner catheter to collapse the expandable filter.

In one aspect of the embolic protection recovery system, the recovery sheath has greater column strength than the inner catheter. As a result, the composite recovery system has reduced stiffness characteristics at the distal end where it would be needed. This particular delivery structure which reduces stiffness helps to improve the trackability of the composite recovery system over the guide wire and through the vasculature, as well.

The method of using the embolic protection recovery system includes loading the inner catheter inside a recovery sheath, wherein the recovery sheath is initially placed over the inner catheter such that a distal portion of the inner catheter extends beyond the distal end of the recovery sheath. The inner catheter can then be introduced over the guide wire having an expanded filter located near the distal end of the guide wire; and advancing the distal end of the inner catheter to a position adjacent to the expanded filter located within the patient's vasculature. The recovery sheath can then by advanced over the distal portion of the inner catheter and over the expanded filter in order to collapse the expanded filter. The recovery sheath, inner sheath, and collapsed filter can then be removed from the vasculature.

It is to be understood that the present invention is not limited by the embodiments described herein. The present invention can be used in arteries, veins, and other body lumens. Other features and advantages of the present invention will become more apparent from the following detailed description of the invention, when taken in conjunction with the accompanying exemplary drawings.

DETAILED DESCRIPTION OF THE PREFERRED EMBODIMENTS

Figure 1:
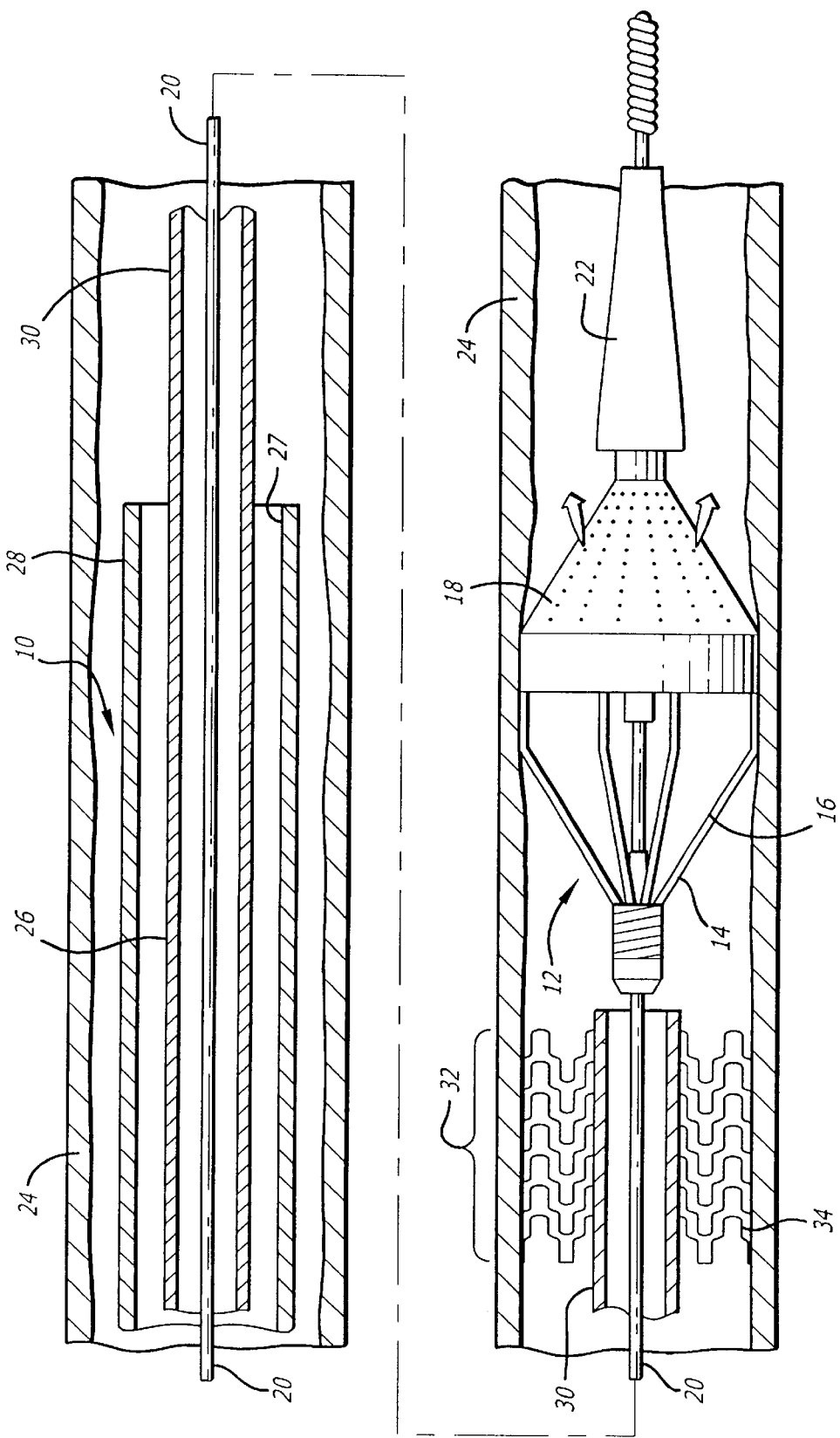
FIG. 1 is a side elevational view, partially in section, of an inner catheter being introduced over a guide wire of an embolic filter device deployed within a body lumen wherein the inner catheter has been loaded inside a recovery sheath.

Referring now to the drawings, wherein like reference numerals denote like or corresponding parts throughout the drawing figures, a recovery system 10 is provided for retrieving an embolic protection device which has been deployed within a body vessel for purposes of capturing embolic material which may be released into a body vessel during a therapeutic interventional procedure. The therapeutic interventional procedure may comprise the implantation of a stent to increase the diameter of an occluded artery and increase the flow of blood therethrough. It should be appreciated that the embodiments of the system and method are illustrated and described herein by way of example only and not by way of limitation. While the present invention is described in detail as applied to an artery of the patient, those skilled in the art will appreciate that it can also be used in body lumens, such as the coronary arteries, carotid arteries, renal arteries, saphenous veins and other peripheral arteries. Additionally, the present invention can be utilized when performing any one of a number of interventional procedures, such as balloon angioplasty, laser angioplasty or atherectomy.

Additional details regarding the particular structure and shape of the embolic protection device are provided below. In the particular embodiment shown in FIGS. 1 through 3, the embolic protection device 12 which has been used to capture embolic debris generated during the intravascular procedure includes a filter assembly 14 having an expandable strut assembly 16 and a filter element 18. The filter assembly 14 is mounted on the distal end of an elongated tubular shaft, such as a guide wire 20. The filter assembly 14 is maintained in a collapsed or compressed position until it is delivered to the treatment site by a delivery catheter (not shown). An obturator 22 affixed to the distal end of the filter assembly 14 can be implemented to prevent possible "snowplowing" of the embolic protection device during delivery through the vasculature. The obturator is made from a soft polymeric material, such as Pebax 40, and has a smooth surface to help the embolic protection device travel through the vasculature and cross lesions while preventing the distal end of the delivery catheter (not shown) from "digging" or "snowplowing" into the wall of the artery 24.

The strut assembly 16 may include self-expanding struts which upon release from the delivery catheter (not shown) expands the filter element 18 into its deployed position within the artery. When the struts are expanded, the filter element 18 takes on a basket shape. Embolic debris created during the interventional procedure and released into the bloodstream are captured within the deployed filter element 18. Once the procedure is completed, the filtering assembly 14 is to be collapsed and removed from the artery 24, along with the embolic debris trapped within the filter element 18. It should be appreciated that the embolic protection device 12 is one example of just one of numerous different embolic protection devices that can be utilized in accordance with the present invention. Generally, the recovery system of the present invention can be utilized in accordance with any embolic protection device which utilizes a filter assembly that can be recovered by collapsing the filter assembly through the advancement of the distal end of a recovery sheath over the struts or other deployment members are utilized to deploy the filter portion of the embolic protection device.

When the embolic protection device 12 is to be removed from the vasculature, the recovery system of the present invention can be utilized. The recovery system 10 includes an inner catheter 26 which is loaded inside a lumen 27 of a recovery sheath 28. The recovery sheath 28 is advanced over the inner catheter 26 and filter assembly 14 to collapse and recover the filter assembly 14. The recovery sheath 28 has a larger inner diameter than the outer diameter of inner catheter 26. The recovery sheath 28 can have a working length approximately 10 to 15 centimeters shorter than the inner catheter 26. This allows a distal portion 30 of the inner catheter 26 to extend beyond the distal end of the recovery sheath 28 during initial delivery through the artery 24, as will be described herein.

The inner catheter 26 is first introduced over the guide wire 20 for delivery past the treatment site 32, where, for example, a stent 34 has been implanted. As shown in FIG. 1, the relatively flexible distal portion 30 of the inner catheter 26 tracks over the guide wire 20 distally to the recovery sheath 28. The inner catheter 26 is less stiff than the recovery sheath 28 and the distal portion 30 of the inner catheter 26 is likely to cause less straightening of the vasculature as it tracks over the guide wire 20 to the expandable filter assembly 14. The delivery of this smaller diameter inner catheter 26 helps to maintain the curvature of the artery by minimizing the possibility of the artery "straightening" as the larger diameter recovery sheath 28 is advanced over the distal portion 30. While the "straightening" effect of the artery is not apparent from the drawings (since the artery 24 is shown relatively straight to begin with), it should be appreciated that this straightening effect would be less likely to occur when the filter assembly is in a curved artery due to the presence of the inner catheter 26. Additionally, the increased flexibility of the inner catheter 26 better enables the distal portion of the inner catheter 26 to negotiate the tortuous anatomy of the vasculature and improves tracking over the guide wire 20. Although not shown, the guide wire 20, inner catheter 26, and recovery sheath 28 have proximal ends which extend outside the patient and are manipulated by the physician to deliver the respective devices to the area of concern.

Figure 2:
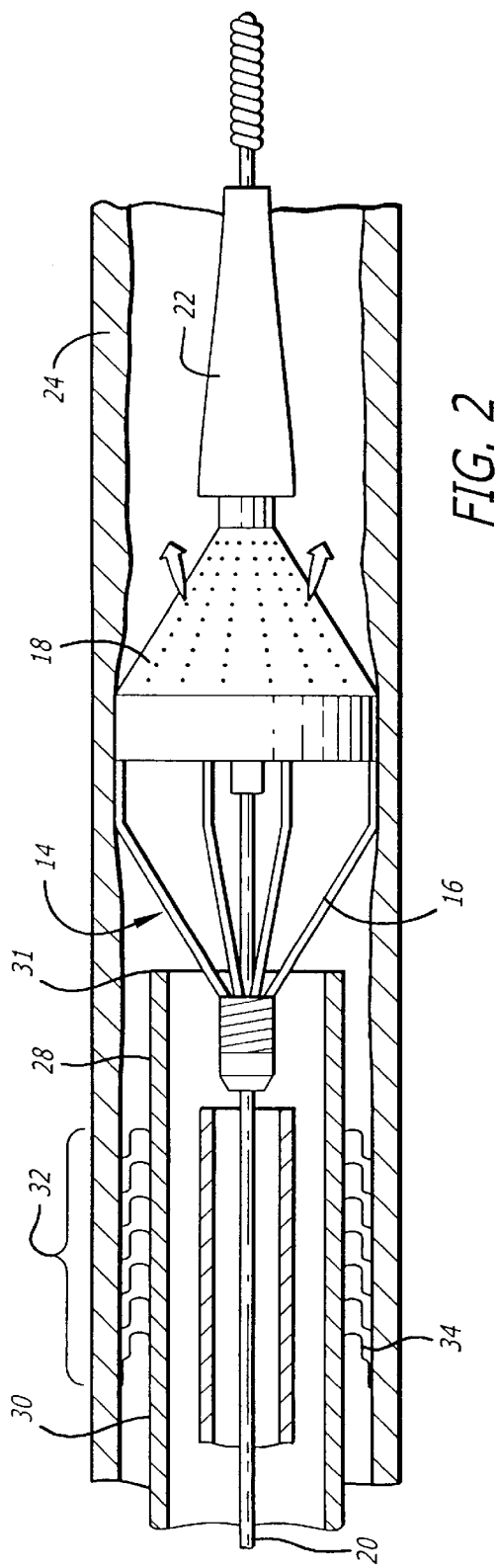
FIG. 2 is a side elevational view, similar to that shown in FIG. 1, wherein the recovery sheath is being advanced over the inner catheter and toward the expanded embolic filter.

As shown in FIG. 2, after the inner catheter 26 has reached the filter assembly 14 past the treatment site 32, the recovery sheath 28 is advanced over the distal portion 30 of the inner catheter 26 and toward the filter assembly 14 in order to collapse and recover the expanded filter assembly 14. The increased column strength at the distal end 31 of the recovery sheath 28 ensures that as the struts of the filter assembly 12 are moved back into its collapsed position, the recovery sheath 28 does not buckle or experience an accordion effect.

Figure 3:
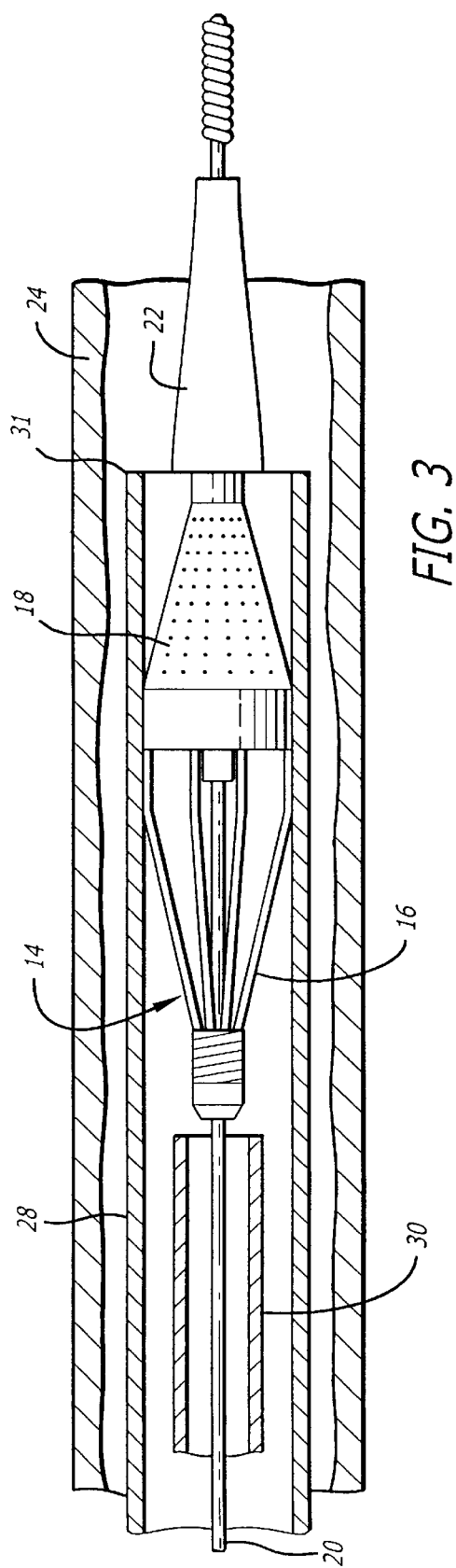
FIG. 3 is a side elevational view, similar to that shown in FIG. 1, wherein the recovery sheath has been advanced over the embolic filter to collapse the filter for removal from the body lumen.

The collapse of the expandable filter assembly 12 can be accomplished by holding the guide wire 20 and, from outside the patient, moving the proximal end of the recovery sheath 28 forward to move the distal end 31 of the sheath 28 over the filter assembly 14. Alternatively, the recovery sheath 28 can be held stationary while the proximal end of the guide wire 20 is retracted back to pull the filter assembly 14 into the recovery sheath 28. Upon collapse of the filter assembly 14, any embolic debris generated during the interventional procedure will remain trapped inside the filter element 18. The recovery system 10, along with the embolic protection device 12, can then be withdrawn from the bloodstream and removed from the vasculature as is shown in FIG. 3.

The materials which can be utilized for the recovery sheath and inner catheter can be made from polymeric material which are well known in the art. One suitable polymeric material is cross-linked HDPE. Alternatively, the recovery sheath and inner catheter can be made from materials such as polyolifin which has sufficient strength to hold the compressed strut assembly and has relatively low frictional characteristics to minimize any friction between the filtering assembly and the sheath. Polyimide could be used for the inner catheter as well. Friction can be further reduced by applying a coat of silicone lubricant, such as Microglide®, to the inside surface of the recovery sheath before the recovery sheath is placed over the filter assembly. Still other suitable materials could be utilized for either the recovery sheath and inner catheter without departing from the spirit and scope of the present invention. Preferably, the wall thickness of the inner catheter is smaller than the recovery sheath to increase the flexibility as the composite recovery sheath/inner catheter is being delivered through the tortuous anatomy. However, depending upon the type of material which is utilized, the wall thickness of the inner catheter could be same or even greater than that of the recovery sheath. As is shown in the drawings, the inner catheter can be made from an elongated tubing which is sufficiently flexible to travel over the guide wire. Other embodiments of the inner catheter can be utilized without departing from the spirit and scope of the present invention.

It should be appreciated that there is a desire to reduce the overall profile of the composite inner catheter/recovery sheath so it would be beneficial to use as small a wall thickness as possible to reduce the profile of the recovery system. However, it should be appreciated that the strength of the recovery sheath still must be sufficient to maintain the filtering assembly of the embolic protection device in a collapsed state for removal from the patient's vasculature.

While illustrated and described herein in terms of its use in the intravascular treatment of arteries, it will be apparent to those skilled in the art that the recovery system can be used in other lumens in the body. Other modifications and improvements may be made without departing from the scope of the invention.

What is claimed is:

1. A system for recovering an embolic protection device which includes a guide wire and expandable filter disposed thereon, comprising:

an inner catheter having a distal portion and being moveable along the guide wire; and a recovery sheath having a distal end, wherein the inner catheter is capable of being loaded inside the recovery sheath with the distal portion of the inner catheter extending distally beyond the distal end of the recovery sheath when the inner catheter and recovery sheath are being advanced along the guide wire for placement in proximity to the expandable filter of the embolic protection device, the recovery sheath having sufficient column strength to collapse the expandable filter when advanced over the expandable filter.

2. The system of claim 1, wherein the recovery sheath is approximately between 10 and 15 centimeters shorter than the inner catheter.

3. The system of claim 1, wherein the recovery sheath is at least 10 centimeters shorter than the inner catheter.

4. The system of claim 1, wherein the recovery sheath has greater column strength than the inner catheter.

5. The system of claim 1, wherein the inner catheter has greater column strength than the recovery sheath.

6. An embolic protection system, comprising:

a guide wire having a distal end;

an expandable filter located near the distal end of the guide wire;

an inner catheter having a distal portion, wherein the inner catheter is capable of being introduced over the guide wire; and a recovery sheath having a distal end, wherein the inner catheter is capable of being loaded inside of a lumen of the recovery sheath, wherein the distal portion of the inner catheter extends distally beyond the distal end of recovery sheath when being advanced along the guide wire to retrieve the expandable filter, the recovery sheath having sufficient column strength to collapse the expandable filter when advanced over the expandable filter.

7. The system of claim 6, wherein the recovery sheath is approximately between 10 and 15 centimeters shorter than the inner catheter.

8. The system of claim 5, wherein the recovery sheath has a greater column strength than the inner catheter.

9. The system of claim 6, wherein the recovery sheath is at least 10 centimeters shorter than the inner catheter.

10. The system of claim 6, wherein the inner catheter has greater column strength than the recovery sheath.

11. A method of recovering an embolic protection device which includes a guide wire and an expandable filter from a body vessel, comprising:

loading an inner catheter inside a recovery sheath, wherein the inner catheter has a distal portion which extends beyond the distal end of the recovery sheath;

introducing the inner catheter and recovery sheath over the guide wire;

advancing the distal end of the inner catheter to a position adjacent to the expanded filter;

advancing the recovery sheath over the distal portion of the inner catheter and the expanded filter to collapse the expanded filter.

12. The method of claim 11, further comprising:

removing the recovery sheath, inner catheter, and embolic protection device from the body vessel.

13. The method of claim 11, wherein the recovery sheath is approximately between 10 and 15 centimeters shorter than the inner catheter.

14. The method of claim 11, wherein the distal portion of the inner catheter extends at least 10 centimeters beyond the distal end of the recovery sheath when being advanced over the guide wire.

15. The method of claim 11, wherein the recovery sheath has greater column strength than the inner catheter.

16. The method of claim 11, wherein the inner catheter is an elongated tubular member.

17. The method of claim 11, wherein the inner catheter has greater column strength than the recovery sheath.

* * * * *

UNITED STATES PATENT AND TRADEMARK OFFICE
CERTIFICATE OF CORRECTION

PATENT NO. : 6,569,184 B2
DATED : May 27, 2003
INVENTOR(S) : Benjamin C. Huter

It is certified that error appears in the above-identified patent and that said Letters Patent is hereby corrected as shown below:

Column 6,
Line 56, change "5", to read -- 6 --.

Signed and Sealed this

Sixteenth Day of September, 2003

JAMES E. ROGAN
*Director of the United States Patent and Trademark Office*